US012558244B2

(12) United States Patent
Sawicki et al.

(10) Patent No.: US 12,558,244 B2
(45) Date of Patent: Feb. 24, 2026

(54) ADJUSTABILITY MECHANISM FOR LOWER LIMB ORTHOSIS

(71) Applicant: Cleveland State University, Cleveland, OH (US)

(72) Inventors: Jerzy T. Sawicki, Westlake, OH (US); Jason J. Wiebrecht, Tallmadge, OH (US); Curt A. Laubscher, Olmsted Township, OH (US); Anthony Goo, Cleveland, OH (US); Ryan J. Farris, Dillsburg, PA (US); Steven J-S Etheridge, Aurora, OH (US)

(73) Assignee: Cleveland State University, Cleveland, OH (US)

( * ) Notice: Subject to any disclaimer, the term of this patent is extended or adjusted under 35 U.S.C. 154(b) by 411 days.

(21) Appl. No.: 18/071,001

(22) Filed: Nov. 29, 2022

(65) Prior Publication Data

US 2024/0173158 A1 May 30, 2024

(51) Int. Cl.
*A61F 5/01* (2006.01)

(52) U.S. Cl.
CPC .......... *A61F 5/0106* (2013.01); *A61F 5/0127* (2013.01); *A61F 2005/0139* (2013.01); *A61F 2005/0146* (2013.01); *A61F 2005/0158* (2013.01)

(58) Field of Classification Search
CPC .. A61F 5/0106; A61F 2005/0139; A61F 5/00; A61F 5/01–34; A61H 1/0237; A61H 1/024; A61H 1/0244; A61H 1/0255
USPC ...................... 602/23; 16/366–371, 221–392
See application file for complete search history.

(56) References Cited

U.S. PATENT DOCUMENTS

| | | | | |
|---|---|---|---|---|
| 6,024,713 A | * | 2/2000 | Barney | .................. A61F 5/0125 |
| | | | | 602/26 |
| 10,130,547 B2 | | 11/2018 | Koren | |
| 10,548,800 B1 | | 2/2020 | Maxwell et al. | |
| 11,207,234 B2 | | 12/2021 | Sawicki et al. | |
| 2008/0078409 A1 | * | 4/2008 | Ciccantelli | ............ A61F 5/0193 |
| | | | | 128/845 |
| 2012/0000092 A1 | * | 1/2012 | Ingvarsson | ........... A61F 5/0111 |
| | | | | 36/88 |
| 2012/0330198 A1 | | 12/2012 | Patoglu | |
| 2013/0178771 A1 | * | 7/2013 | Moir | ..................... A61F 5/0123 |
| | | | | 602/16 |
| 2015/0088043 A1 | * | 3/2015 | Goldfield | .................. A61F 5/01 |
| | | | | 602/6 |
| 2015/0272810 A1 | * | 10/2015 | Teng | .................... A61H 1/0244 |
| | | | | 601/34 |
| 2017/0340504 A1 | | 11/2017 | Sanz Merodio et al. | |

(Continued)

FOREIGN PATENT DOCUMENTS

RU        2725288 C2    6/2020

*Primary Examiner* — Keri J Nelson
*Assistant Examiner* — Seth R. Brown
(74) *Attorney, Agent, or Firm* — Calfee, Halter & Griswold LLP

(57) ABSTRACT

An actuating assembly including a first actuating device, a second actuating device, and an adjustment mechanism. The first actuating device is configured to provide an output torque to a first portion of a user, and the second actuating device is configured to provide an output torque to a second portion of the user. The adjustment mechanism is connected to the first and second actuating devices. The adjustment mechanism is configured to adjust a distance between the first and second actuating devices.

5 Claims, 13 Drawing Sheets

(56)     References Cited

U.S. PATENT DOCUMENTS

2019/0192372 A1     6/2019  Little et al.
2019/0209414 A1*    7/2019  Etheridge ............. A61H 1/024
2019/0254854 A1*    8/2019  Lee ..................... A61H 1/0237
2021/0369543 A1    12/2021  Etheridge et al.

* cited by examiner

ADJUSTABILITY MECHANISM FOR LOWER LIMB ORTHOSIS

CROSS-REFERENCE TO RELATED APPLICATIONS

This non-provisional application does not claim priority to another application.

FIELD OF DISCLOSURE

This disclosure relates generally to actuating assemblies for orthosis and, more particularly, to actuating assemblies for lower limb orthosis.

BACKGROUND

Temporary or permanent injuries or disabilities, or both, may affect a person's ability to walk, especially with a healthy gait. To help rehabilitate or assist such persons to walk with a healthy gait, a lower limb orthosis is used to provide torque to the lower limbs (e.g., hips, knees, etc.) of an individual.

Typical lower limb orthoses include one or more actuating arms or members, where each actuating arm or member has an axis of rotation that substantially aligns with the corresponding axis of rotation of the lower limb to which it provides torque. In some instances, a thigh powered orthosis device may include a first actuating arm for engaging a hip of a user and a second actuating arm for engaging a knee of the user.

SUMMARY

The general inventive concepts are directed to an actuating assembly for a powered lower limb orthosis that is configured to rehabilitate or assist a person who is walking impaired. A lower limb orthosis is a device used to help assist, rehabilitate, and/or improve disorders of a person's lower limbs (e.g., a person's hip or knee). In certain embodiments, an orthosis utilizing the actuating device may be configured to provide assistive or rehabilitative torque to the lower limbs of the user. Also, the orthosis may be configured to provide torque to aid a paralyzed or otherwise disabled person in walking.

An example of an actuating assembly includes a first actuating device, a second actuating device, and an adjustment mechanism. The first actuating device is configured to provide an output torque to a first portion of a user, and the second actuating device is configured to provide an output torque to a second portion of the user. The adjustment mechanism is connected to the first and second actuating devices. The adjustment mechanism is configured to adjust a distance between the first and second actuating devices.

Another example of an actuating assembly includes a first actuating device, a second actuating device, and an adjustment mechanism. The first actuating device is configured to provide an output torque to a first portion of a user, and the second actuating device is configured to provide an output torque to a second portion of the user. The adjustment mechanism is configured to adjust a distance between the first and second actuating devices. The adjustment mechanism includes first and second scissor arms, first and second threaded nuts, first and second threaded rods, and a gear. The first scissor arm has a first arm portion and a second arm portion that are pivotally connected at a first connection point, where the first arm portion is connected to the first actuating device and the second arm portion is connected to the second actuating device. The second scissor arm has a third arm portion and a fourth arm portion that are pivotally connected at a second connection point, where the third arm portion is connected to the first actuating device and the fourth arm portion is connected to the second actuating device. The first threaded nut is connected to the first scissor arm at the first connection point, and the second threaded nut is connected to the second scissor arm at the second connection point. The first threaded rod is connected to the first threaded nut such that rotation of the first threaded rod causes the first threaded nut to move along a length of the first threaded rod, and the second threaded rod is connected to the second threaded nut such that rotation of the second threaded rod causes the second threaded nut to move along a length of the second threaded rod. The gear is connected to the first and second threaded rods such that rotation of the gear causes the first and second threaded rods to rotate.

Another example of an actuating assembly includes a first actuating device, a second actuating device, and an adjustment mechanism. The first actuating device is configured to provide an output torque to a first portion of a user, and the second actuating device is configured to provide an output torque to a second portion of the user. The adjustment mechanism is configured to adjust a distance between the first and second actuating devices. The adjustment mechanism includes a first rack, a second rack, a first gear, a second gear, and a rod. The first rack has a first member and a second member, where the first member is fixedly connected to the first actuating device and the second member is fixedly connected to the second actuating device. The second rack has a third member and a fourth member, wherein the third member is fixedly connected to the second actuating device and the fourth member is fixedly connected to the first actuating device. The first gear is connected to the first rack, the second gear is connected to the second rack, and the rod is connected to and extending between the first and second gears.

BRIEF DESCRIPTION OF THE DRAWINGS

The general inventive concepts, as well as embodiments and advantages thereof, are described below in greater detail, by way of example, with reference to the drawings in which.

DETAILED DESCRIPTION

Figure 1:
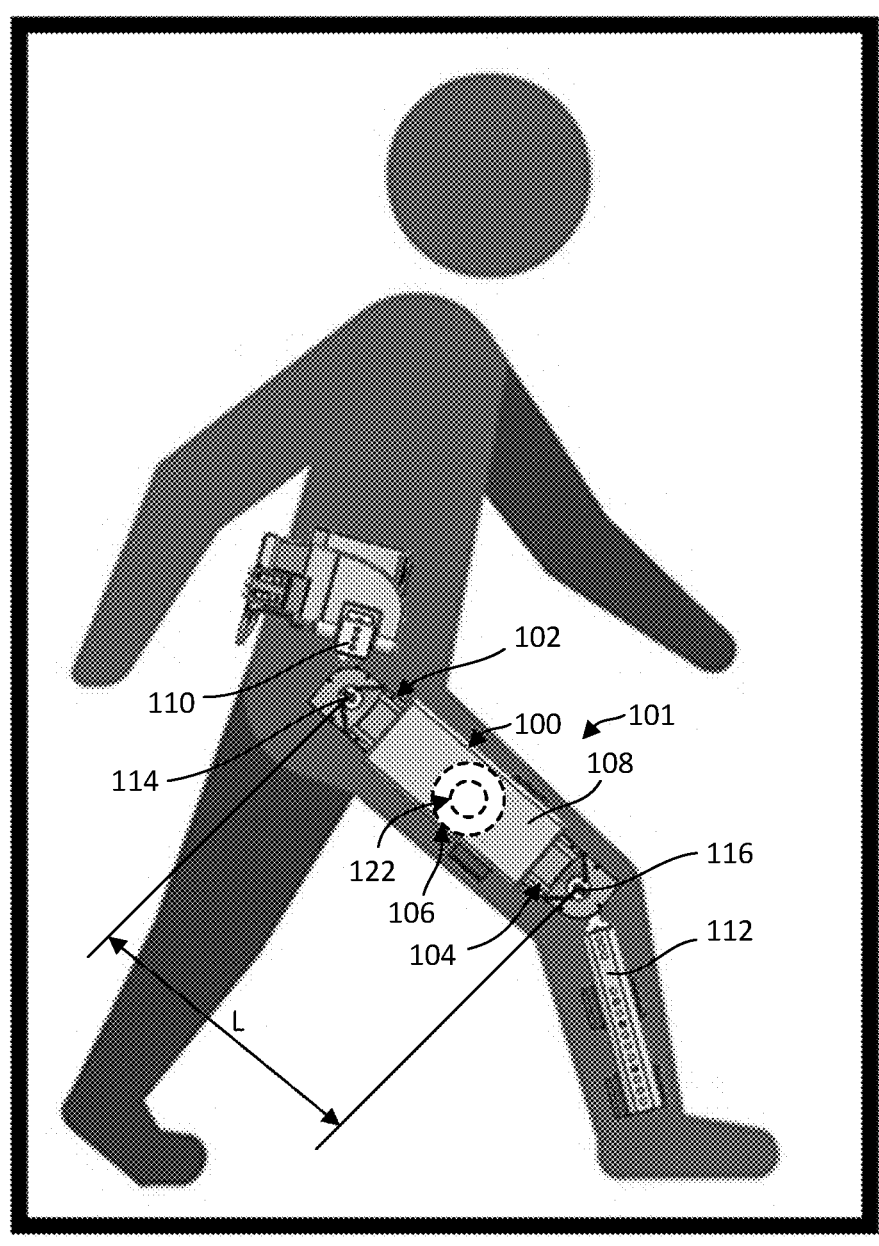
FIG. 1 illustrates a side view of a user with an example powered lower limb orthosis according to the general inventive concepts.

The following describes exemplary embodiments according to the general inventive concepts and is not intended to limit the scope of the claims in any way. The terms used in the claims have their full ordinary meaning.

While certain exemplary embodiments described herein and illustrated in the drawings relate to an adjustability mechanism for lower limb orthosis (e.g., powered lower limb orthosis), it should be understood that many of the inventive features described herein may be applied to other devices, systems, and methods. For example, the features described herein may be utilized in other types of orthosis devices, including upper limb orthosis.

The present application is directed to an actuating assembly for a powered lower limb orthosis that is configured to rehabilitate or assist a person who is walking impaired. A lower limb orthosis is a device used to help assist, rehabilitate, and/or improve disorders of a person's lower limbs (e.g., a person's hip or knee) or ambulation. In certain embodiments, an orthosis utilizing the actuating assembly may be configured to provide assistive or rehabilitative torque to the lower limbs of the user. Also, the orthosis may be configured to provide torque to aid a paralyzed or otherwise disabled person in walking.

An orthosis or actuating assembly may include one or more actuating devices (also called "cassettes" or "cartridges") that are configured to supply torque to the hip(s), knee(s), ankle(s), or any combination of the hip(s), knee(s), and ankle(s) of a user. In certain embodiments, the actuating assembly aids in rehabilitating a user's gait by guiding the user's walking to a healthy gait. In addition, the actuating assembly may be configured to assist a walking user by decreasing the user's necessary exertion on one or more limbs of the user. In an exemplary embodiment, the actuating assembly may be configured to aid and assist the gait of the walking impaired pediatric population (i.e., children between the ages 6 and 11). However, the actuating assembly may be used in several other applications that require the described features, such as, for example, providing performance improving torque to the lower limbs of healthy individuals, as a joint actuator in an upper limb orthosis where quiet operation is needed, as a joint actuator in service robots where quiet operation is needed, or any other suitable application.

The actuating assemblies of the present application provide a powered lower limb orthosis with several advantages over existing lower limb orthosis. For example, the actuating assemblies described herein have an adjustment mechanism that allows for easy adjustment of a length of the actuating assembly based on a size of the user. While some actuating assemblies for orthosis devices are adjustable, the devices typically require a user to remove components (e.g., fasteners, housing, etc.) to make adjustments. The adjustment mechanisms described here allow for a user to make quick adjustments. In some implementations, the adjustment mechanisms described herein allow a user to make adjustments to the actuating assembly while the actuating assembly is being worn by a user. Some of the adjustment mechanisms described herein are operated using external powered or unpowered tooling. Some of the adjustment mechanisms described herein do not require such tooling. The adjustment mechanisms described in the present application are advantageous for the walking impaired pediatric population (i.e., children between the ages 6 and 11) because this population typically grows significantly during use of such devices, and the adjustment mechanisms described herein allow a user to easily adjust the length of such devices to accommodate for changes in gait or growth of the child.

Referring to FIGS. 1-4, an example actuating assembly 100 for powered orthosis system 101 includes a first actuating device 102, a second actuating device 104, and an adjustment mechanism 106 (FIG. 1) connected to both of the first and second actuating devices. The first and second actuating devices 102, 104 can take any suitable form that is capable of supplying an output torque to the hip(s), knee(s), ankle(s), or any combination of the hip(s), knee(s), and ankle(s) of a user. For example, the first and second actuating devices 102, 104 can take the form of any of the actuating devices described in U.S. Pat. No. 11,207,234 ("the '234 patent"), which is incorporated herein by reference in its entirety. In various implementations, the actuating assembly 100 includes a housing 108 that at least partially houses one or more of the first actuating device 102, the second actuating device 104, and the adjustment mechanism 106.

In certain implementations, the first actuating device 102 has a first actuating arm 110 that engages a hip region of a user, and the second actuating device 104 has a second actuating arm 112 that engages a knee region of the user. The first actuating arm 110 can have a rotational axis 114 that is configured to align with a rotational axis of the user's hip (as shown in FIG. 1), and the second actuating arm 112 can have a rotational axis 116 that is configured to align with a rotational axis of the user's knee (as shown in FIG. 1).

The adjustment mechanism 106 (FIG. 1) is configured to move the first and second actuating devices 102, 104 relative to each other such that the rotational axes 114, 116 of the corresponding actuating arms 110, 112 move relative to each other. That is, the adjustment mechanism 106 allows for adjustment of the length L (FIG. 1) between the rotational axes 114, 116. This adjustment capability is advantageous because it allows for adjustment of the actuating assembly 100 based on the growth of a user. For example, members the pediatric population typically grow significantly between ages of 6 and 11 and, because the rotational axes 114, 116 of the actuating arms 110, 112 are to be substantially aligned with the rotational axes of the user's hip and knee, respectively, the adjustment mechanism 106 allows for adjustment of the length L between the rotational axes 114, 116 to account for such growth. The length L can be adjusted to be between about 26 cm and about 40 cm, such as between about 29 cm and about 37 cm.

Figures 3, 4:
FIG. 3 is a perspective view of an example actuating assembly that can be used with powered lower limb orthosis, where the actuating assembly is in a narrowed configuration.
FIG. 4 is a perspective view of the actuating assembly of FIG. 3, where the actuating assembly is in an extended configuration.

The adjustment mechanism 106 can be connected to the first actuating device 102 and/or the second actuating device 104 such that one or both of the actuating devices 102, 104 can be moved by the adjustment mechanism 106. For example, in various implementations, the adjustment mechanism 106 can be operatively connected to each of the actuating devices 102, 104 and configured to simultaneously move the actuating devices 102, 104 relative to each other. That is, the adjustment mechanism 106 can move the actuating assembly 100 from a narrowed configuration (as shown in FIG. 3) to an extended configuration (as shown in FIG. 4) by causing the first actuating device 102 to move in an outward direction X1 and causing the second actuating device 104 to move in an outward direction X2. The adjustment mechanism 106 can then move the actuating assembly 100 from the extended configuration (as shown in FIG. 4) to the narrowed configuration (as shown in FIG. 3) by causing the first actuating device 102 to move in an inward direction Y1 and causing the second actuating device 104 to move in an inward direction Y2.

In other implementations, the adjustment mechanism 106 may only be configured to move the first actuating device 102 relative to the second actuating device 104, but not be configured to move the second actuating device 104. For example, the adjustment mechanism 106 can be configured to move the actuating assembly 100 from the narrowed position (as shown in FIG. 3) to the extended position (as shown in FIG. 4) by only moving the first actuating device 102 in the direction X1, but the adjustment mechanism 106 is not configured to move the second actuating device 104 in the direction X2. Alternatively, the adjustment mechanism 106 may only be configured to move the second actuating device 104 relative to the first actuating device 102, but not be configured to move the first actuating device 102. For example, the adjustment mechanism 106 can be configured to move the actuating assembly 100 from the narrowed position (as shown in FIG. 3) to the extended position (as shown in FIG. 4) by only moving the second actuating device 104 in the direction X2, but the adjustment mechanism 106 is not configured to move the first actuating device 102 in the direction X1. In some implementations, the adjustment mechanism 106 may be configured to move both of the actuating devices 102, 104 independently relative to each other rather than only simultaneous movement.

The adjustment mechanism 106 may include a gear and scissor mechanism (e.g., similar to the adjustment mechanism 206 shown in FIGS. 5-10), a dual rack and pinion mechanism (e.g., similar to the adjustment mechanism 306 shown in FIGS. 11-14) or any other suitable components for an adjustment mechanism. The adjustment mechanism 106 can be configured to be driven by an external tool or component (e.g., similar to the adjustment mechanism 206 shown in FIGS. 5-10). The tool or component for driving the adjustment mechanism 106 can be, for example, a screwdriver, a powered hex key, an unpowered hex key, or any other suitable tool or component that is capable of driving the adjustment mechanism 106. In other implementations, the adjustment mechanism 106 can be non-driven such that it does not require an external tool or component to control the adjustment mechanism.

Referring to FIG. 3, a length L1 may extend between the rotational axis 114 of the first actuating arm 110 of the first actuating device 102 and the rotational axis 116 of the second actuating arm 112 of the second actuating device 104 when the actuating assembly 100 is in a fully narrowed position. The length L1 can be between about 26 cm and about 30 cm, such as between about 26 cm and about 27 cm or between about 29 cm and about 30 cm. Referring to FIG. 4, a length L2 may extend between the rotational axis 114 of the first actuating arm 110 of the first actuating device 102 and the rotational axis 116 of the second actuating arm 112 of the second actuating device 104 when the actuating assembly 100 is in a fully extended position. The length L2 can be between about 36 cm and about 40 cm, such as between about 36 cm and about 37 cm or between about 39 cm and about 40 cm. In certain implementations, the adjustable length of the adjustment mechanism 106 (i.e., the difference between the length L2 and the length L1) can be between about 6 cm and about 14 cm, such as between 6 cm and about 8 cm or between about 12 cm and about 14 cm.

In implementations that include the housing 108, the housing 108 can at least partially house one or more of the first actuating device 102, the second actuating device 104, and the adjustment mechanism 106. In various of these implementations, the adjustment mechanism 106 can be configured to move one or both of the actuating devices 102, 104 relative to the housing 108. For example, the adjustment mechanism 106 can be configured to move the first actuating device 102 through the opening 118 of the housing 108 when moving the actuating assembly 100 between a narrowed position (as shown in FIG. 3) and an extended position (as shown in FIG. 4), and/or the adjustment mechanism 106 can be configured to move the second actuating device 104 through the opening 120 of the housing 108 when moving the actuating assembly 100 between a narrowed position and an extended position. In implementations that require external tooling to drive the adjustment mechanism 106, the housing may include one or more additional openings (not shown) that allow for a user to engage the adjustment mechanism 106 with the external tooling.

In certain implementations, the actuating assembly 100 includes a locking mechanism 122 for locking the actuating assembly 100 at a desired length for the user. The locking mechanism 122 can take any suitable form, such as, for example, any form for a locking mechanism described in the present application.

Figure 2:
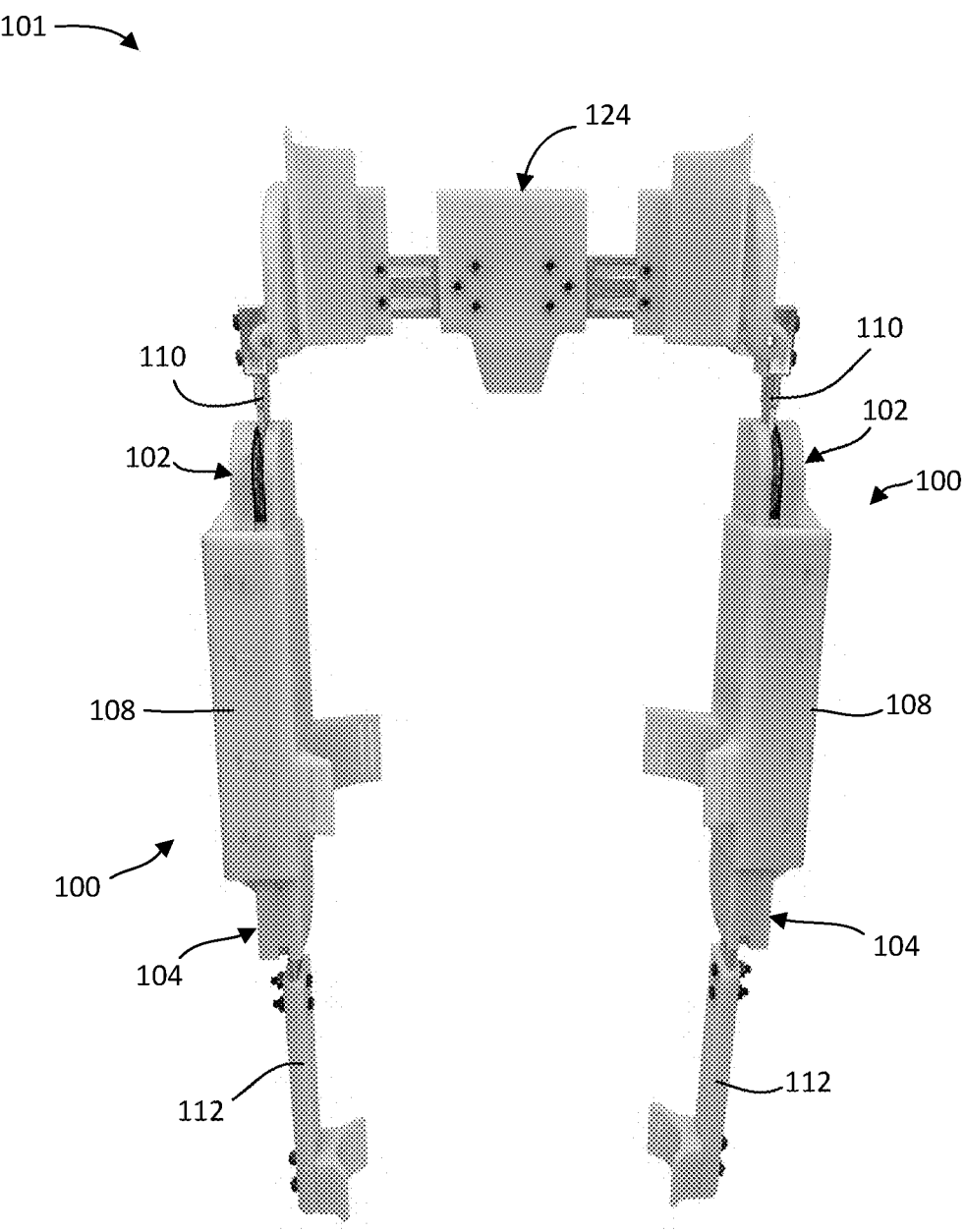
FIG. 2 is a front view of the powered lower limb orthosis of FIG. 1.

Referring to FIG. 2, a powered orthosis system 101 can include multiple actuating assemblies 100. For example, a user may require an actuating assembly 100 for each leg. In the illustrated implementation, the powered orthosis system 101 includes two actuating assemblies 100 and a connection element 124 that connects the two actuating assemblies 100 and extends around a hip portion of the user. Each of the actuating assemblies 100 can take any suitable form, such as, for example, any form for an actuating assembly described in the present application.

Referring to FIGS. 5-10, an example actuating assembly 200 for powered orthosis includes a first actuating device 202, a second actuating device 204, and an adjustment mechanism 206 connected to both of the first and second actuating devices. The first and second actuating devices 202, 204 can take any suitable form that is capable of supplying an output torque to the hip(s), knee(s), ankle(s), or any combination of the hip(s), knee(s), and ankle(s) of a user. For example, the first and second actuating devices 202, 204 can take the form of any of the actuating devices described in the '234 patent, which is incorporated herein by reference in its entirety. In various implementations, the actuating assembly 200 can include a housing 208 that at least partially houses one or more of the first actuating device 202, the second actuating device 204, and the adjustment mechanism 206.

The first actuating device 202 can have a first actuating arm (not shown) that engages a hip region of a user, and the second actuating device 204 has a second actuating arm (not shown) that engages a knee region of the user. The first actuating arm can have a rotational axis 214 that is configured to align with a rotational axis of the user's hip, and the second actuating arm can have a rotational axis 216 that is configured to align with a rotational axis of the user's knee.

The adjustment mechanism 206 is configured to move the first and second actuating devices 202, 204 relative to each other such that the rotational axes 214, 216 of the corresponding actuating arms move relative to each other. That is, the adjustment mechanism 206 allows for adjustment of the length L (FIG. 5) between the rotational axes 214, 216. This adjustment capability is advantageous because it allows for adjustment of the actuating assembly 200 based on the growth of a user. For example, members the pediatric population typically grow significantly between ages of 6 and 11 and, because the rotational axes 214, 216 of the actuating arms are to be substantially aligned with the rotational axes of the user's hip and knee, respectively, the adjustment mechanism 206 allows for adjustment of the length L between the rotational axes 214, 216 to account for such growth. The length L can be adjusted to be between about 26 cm and about 40 cm, such as between about 29 cm and about 37 cm.

In the illustrated implementation, the adjustment mechanism 206 is a gear and scissor mechanism that includes a first scissor arm 230, a second scissor arm 232, a first threaded rod 234, a second threaded rod 236, and a gear 238. The first scissor arm 230 includes a first arm portion 240, a second arm portion 242 pivotally connected to the first arm portion 240, and a first threaded nut 244 (FIGS. 9-10) positioned at the pivotal connection 252 between the first and second arm portions. The first threaded rod 234 extends through and is connected to the first threaded nut 244 (FIGS. 9-10) such that rotation of the first threaded rod 234 causes the first threaded nut 244 to move along a length of the first threaded rod 234. The second scissor arm 232 includes a first arm portion 246, a second arm portion 248 pivotally connected to the first arm portion 246, and a second threaded nut 250 positioned at the pivotal connection 254 between the first and second arm portions of the second scissor arm 232. The second threaded rod 236 extends through and is connected to the second threaded nut 250 such that rotation of the second threaded rod 236 causes the second threaded nut

250 to move along a length of the second threaded rod 236. In the illustrated implementation, each arm portion 240, 242, 246, 248 includes a pair of elongated members with the corresponding threaded nut 244, 250 and threaded rod 234, 236 positioned between the elongated members. However, it should be understood that each arm portion 240, 242, 246, 248 can include any suitable number of elongated members.

The first arm portions 240, 246 of the first and second scissor arms 230, 232, respectively, are pivotally attached to the first actuating device 202, and the second arm portions 242, 248 of the first and second scissor arms 230, 232, respectively, are pivotally attached to the second actuating device 204. The arm portions of the first and second scissor arms 230, 232 can be pivotally attached to the first and second actuating devices 202, 204 by any suitable means.

Figure 6:
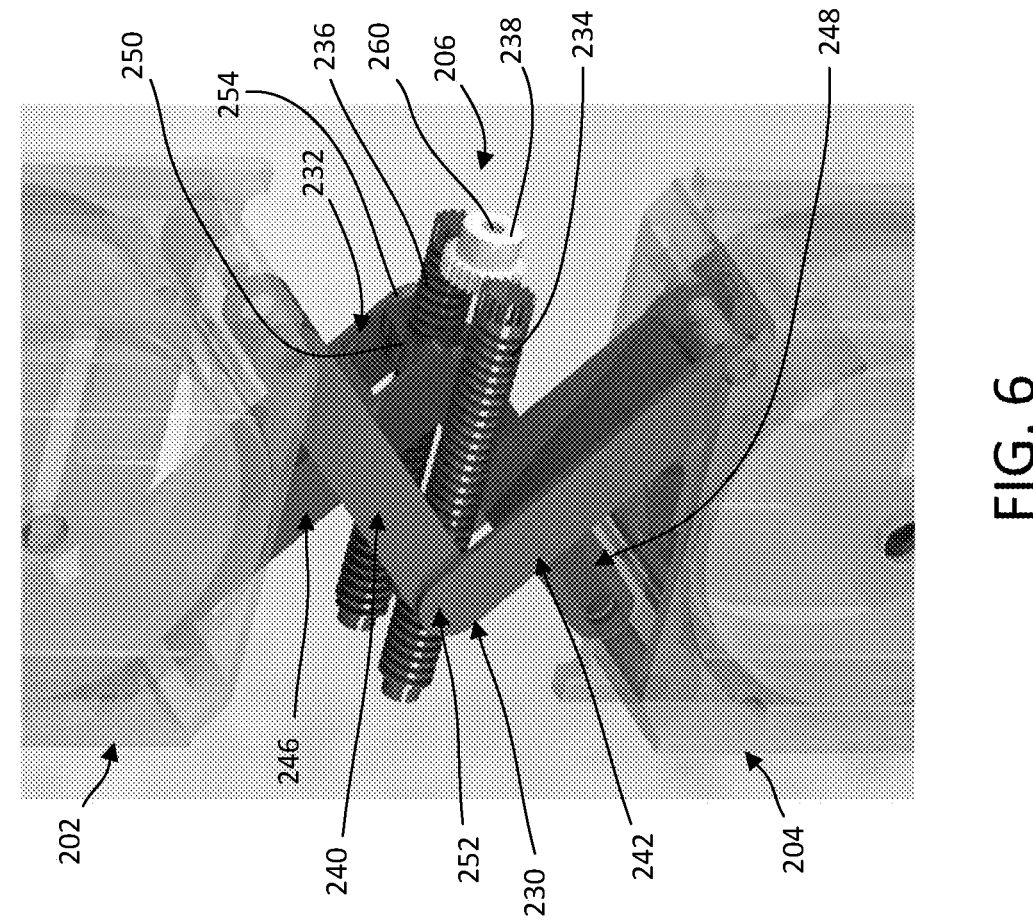
FIG. 6 is a magnified perspective view of the adjustment mechanism of FIG. 5.
Figure 5:
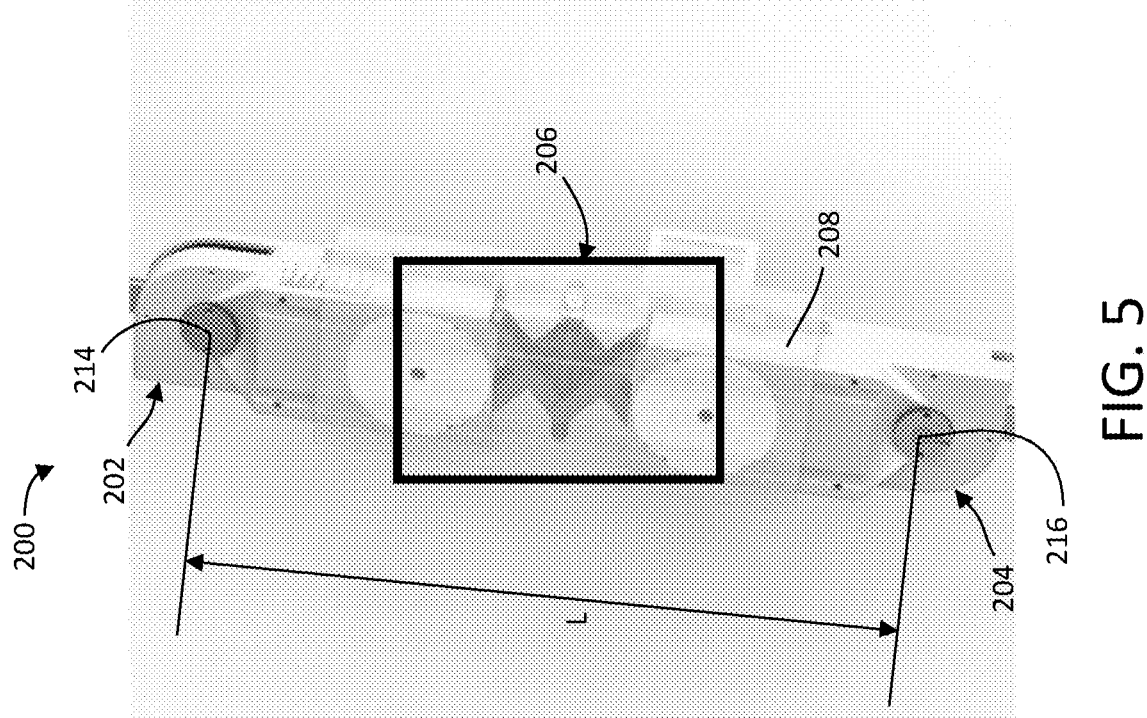
FIG. 5 is a perspective view of another example actuating assembly having an example adjustment mechanism for moving the actuating assembly between narrowed and extended configurations.

Referring to FIG. 6, the gear 238 is positioned between and in rotational communication with the first and second threaded rods 234, 236 such that rotation of the gear 238 causes the threaded rods 234, 236 to rotate. The gear 238 can have a hole 260 for receiving an external tool or component such that a user can cause the gear 238 to rotate. The hole 260 can be aligned with an opening (not shown) of the housing 208 such that a user can engage the gear 238 with an external tool or component. In the illustrated example, the hole 260 has a hexagonal shape, but it should be understood that the hole 260 can have any other polygonal shape or any other shape that allows for an external tool or component to be inserted into the hole 260 to allow a user to rotate the gear 238. In some implementations, the gear 238 is attached to a component (e.g., a knob or the like) of the actuating assembly 200 that allows a user to rotate the gear 238.

In an implementation, rotation of the gear 238 in a clockwise direction causes both of the first and second threaded rods 234, 236 to rotate in the counterclockwise direction, and rotation of the gear 238 in the clockwise direction causes both of the first and second threaded rods 234, 236 to rotate in the counterclockwise direction. The threading direction of the first threaded rod 234 and the first threaded nut 244 is opposite the threading of the second threaded rod 236 and the second threaded nut 250 such that rotation of the gear 238 causes the threaded nuts 244, 250 to move in opposite directions. For example, the first threaded rod 234 and threaded nut 244 may have a counterclockwise thread and the second threaded rod 236 and threaded nut 250 may have a clockwise thread. In this example, rotation of the gear 238 in the clockwise direction causes the actuating assembly 200 to move to an expanded configuration, and rotation of the gear 238 in the counterclockwise direction causes the actuating assembly 200 to move to a narrowed configuration. In other implementations, the first threaded rod 234 and threaded nut 244 may have a clockwise thread and the second threaded rod 236 and threaded nut 250 may have a counterclockwise thread. In this implementation, rotation of the gear 238 in the clockwise direction causes the actuating assembly 200 to move to a narrowed configuration, and rotation of the gear 238 in the counterclockwise direction causes the actuating assembly 200 to move to an expanded configuration.

Figure 7:
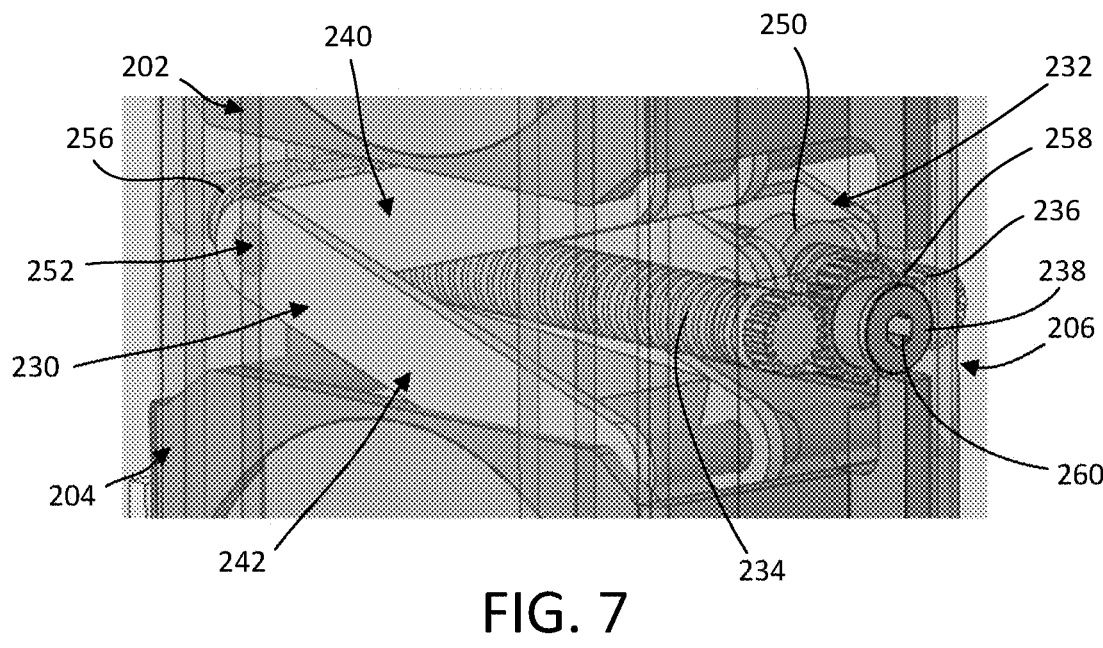
FIG. 7 illustrates a perspective view of the adjustment mechanism in FIG. 5, where the adjustment mechanism is in a first configuration.
Figure 8:
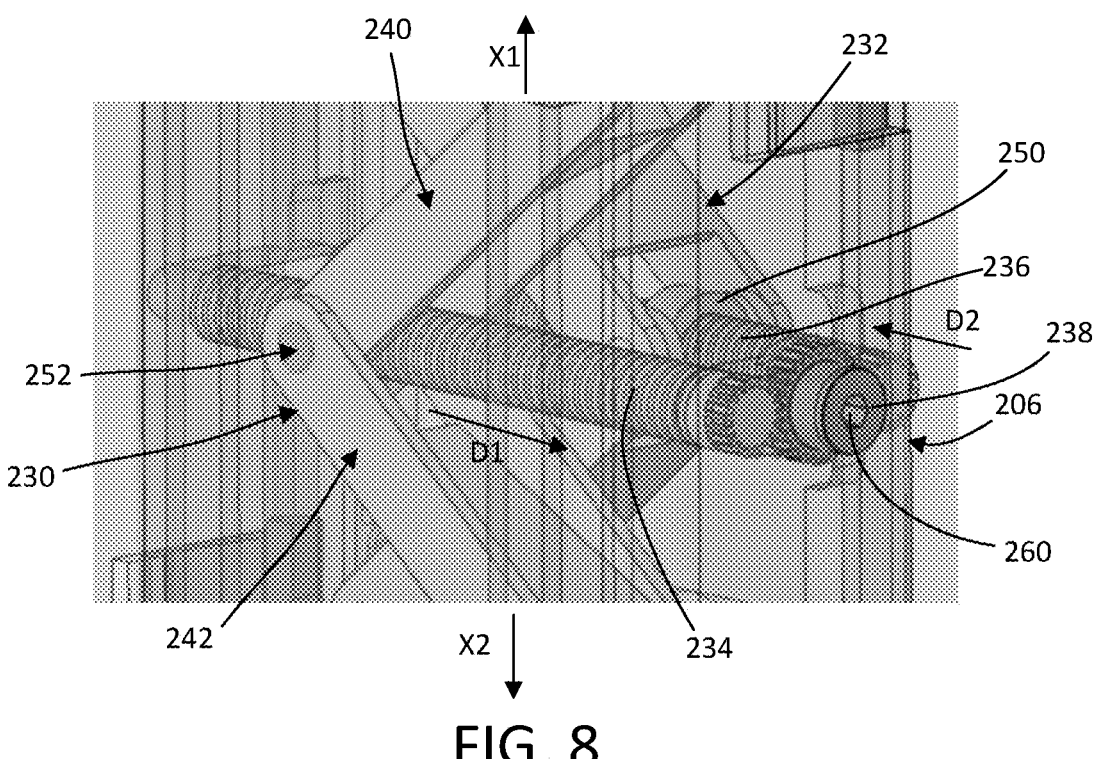
FIG. 8 illustrates a perspective view of the adjustment mechanism of FIG. 5, where the adjustment mechanism is in a second configuration.

Referring to FIG. 7, the adjustment mechanism 206 is shown in a first configuration that causes the actuating assembly 200 (FIG. 5) to be in a substantially narrowed configuration. When in the first configuration, the first threaded nut 244 (FIGS. 9-10) at the pivotal connection 252 is proximate a first end 256 of the first threaded rod 234, and the second threaded nut 250 is proximate a second end 258 of the second threaded rod 236. Referring to FIG. 8, rotation of the gear 238 in the clockwise direction causes the adjustment mechanism 206 to move from the first configuration to a second configuration. That is, this clockwise rotation of the gear 238 causes the first threaded nut 244 to move in a direction D1 and causes the second threaded nut 250 to move in a direction D2, which causes the first and second scissor arms to open due to the movement of the pivotal connections 252, 254 (resulting from the connection between the threaded nuts 244, 250 and the corresponding scissor arms 230, 232 at the pivotal connections 252, 254). This movement of the scissor arms 230, 232 causes the actuating assembly 200 to lengthen by causing the first actuating device 202 to move in the direction X1 and the second actuating device 204 to move the direction X2, as compared to the positioning of the actuating assembly 200 when the adjustment mechanism 206 is in the first configuration shown in FIG. 7.

Figures 9, 10:
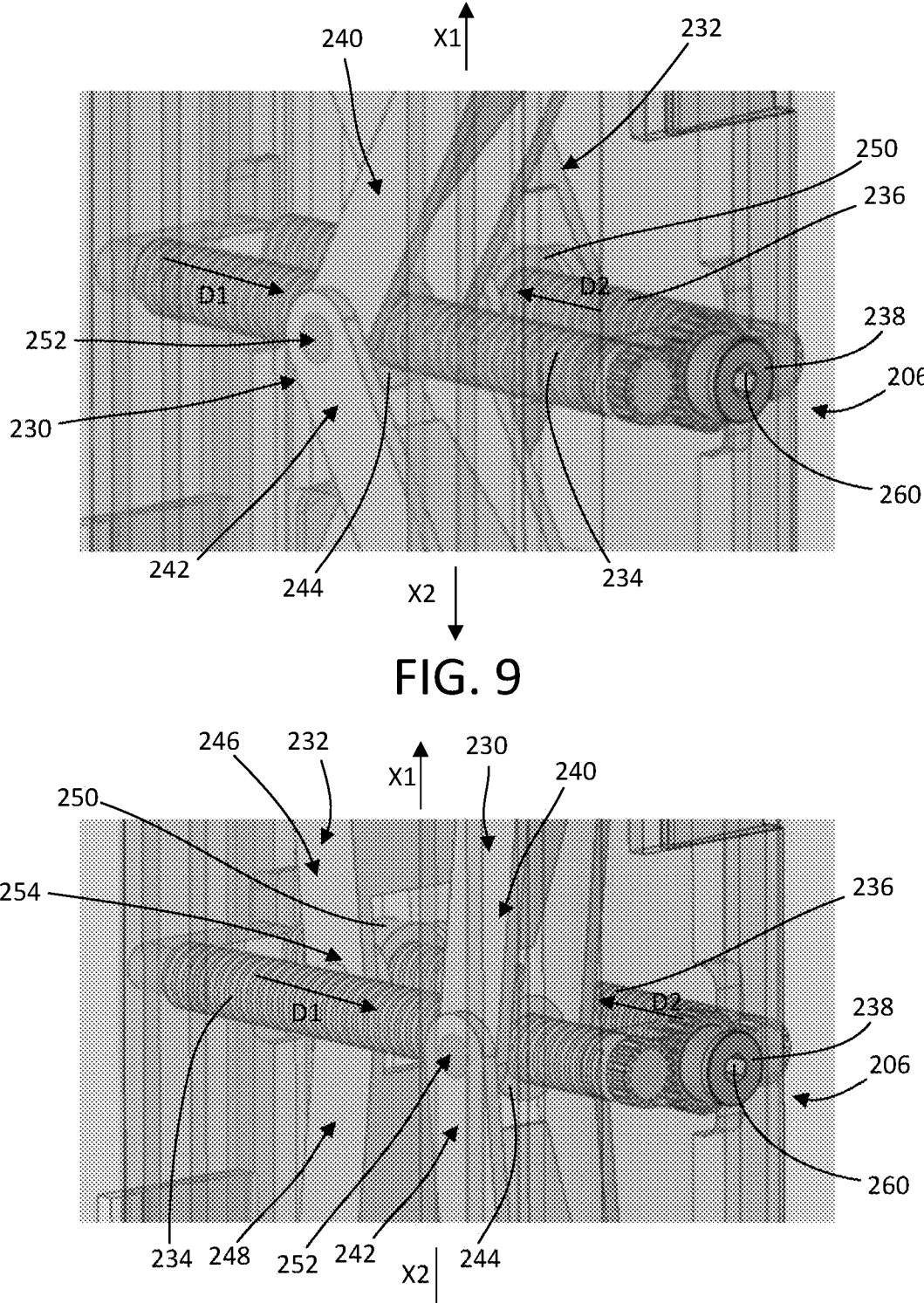
FIG. 9 illustrates a perspective view of the adjustment mechanism of FIG. 5, where the adjustment mechanism is in a third configuration.
FIG. 10 illustrates a perspective view of the adjustment mechanism of FIG. 5, where the adjustment mechanism is in a fourth configuration.

Referring to FIG. 9, further rotation of the gear 238 in the clockwise direction causes the adjustment mechanism 206 to move from the second configuration to a third configuration. That is, this continued clockwise rotation of the gear 238 causes the first threaded nut 244 to further move in the direction D1 and causes the second threaded nut 250 to further move in the direction D2, which causes the first and second scissor arms to further open due to the movement of the pivotal connections 252, 254 (resulting from the connection between the threaded nuts 244, 250 and the corresponding scissor arms 230, 232 at the pivotal connections 252, 254). This movement of the scissor arms 230, 232 causes the actuating assembly 200 to lengthen by causing the first actuating device 202 to further move in the direction X1 and the second actuating device 204 to further move the direction X2, as compared to the positioning of the actuating assembly 200 when the adjustment mechanism 206 is in the second configuration shown in FIG. 8.

Referring to FIG. 10, further rotation of the gear 238 in the clockwise direction causes the adjustment mechanism 206 to move from the third configuration to a fourth configuration. That is, this continued clockwise rotation of the gear 238 causes the first threaded nut 244 to further move in the direction D1 and causes the second threaded nut 250 to further move in the direction D2, which causes the first and second scissor arms to further open due to the movement of the pivotal connections 252, 254 (resulting from the connection between the threaded nuts 244, 250 and the corresponding scissor arms 230, 232 at the pivotal connections 252, 254). This movement of the scissor arms 230, 232 causes the actuating assembly 200 to lengthen by causing the first actuating device 202 to further move in the direction X1 and the second actuating device 204 to further move the direction X2, as compared to the positioning of the actuating assembly 200 when the adjustment mechanism 206 is in the third configuration shown in FIG. 9.

While FIGS. 7-10 show the adjustment mechanism 206 being moved from a narrowed configuration to an extended configuration, it should be understood that the adjustment mechanism 206 can be narrowed from any configuration (e.g., in the illustrated implementation by rotating the gear 238 in a counterclockwise direction) until it reaches one or more of the more narrowed configurations, and the adjustment mechanism 206 can be extended from any configuration (e.g., in the illustrated implementation by rotating the gear 238 in a clockwise direction) until it reaches one or more of the extended configurations. It should also be understood that the adjustment mechanism 206 can be stopped such that the actuating assembly can be at any length between a fully narrowed configuration and a fully extended configuration. While the illustrated examples show a clockwise rotation of the gear 238 causes the adjustment mechanism 206 to move to an extended configuration and a counterclockwise rotation of the gear 238 causes the adjustment mechanism 206 to move to a narrowed configuration, those of ordinary skill in the art will understand that the adjustment mechanism 206 can be configured such that a counterclockwise rotation of the gear 238 causes the adjustment mechanism 206 to move to an extended configuration and a clockwise rotation of the gear 238 causes the adjustment mechanism 206 to move to a narrowed configuration.

The length L (FIG. 5) extending between the rotational axis 214 of the first actuating arm of the first actuating device 202 and the rotational axis 216 of the second actuating arm of the second actuating device 204 may have a length of between about 26 cm and about 30 cm, such as between about 26 cm and about 27 cm or between about 29 cm and about 30 cm, when the actuating assembly 200 is in a fully narrowed (or shortest) configuration. This length L may be between about 36 cm and about 40 cm, such as between about 36 cm and about 37 cm or between about 39 cm and about 40 cm, when the actuating assembly 200 is in a fully extended (or longest) configuration. In certain implementations, the adjustable length of the adjustment mechanism 206 (i.e., the difference between the length L when in the fully extended configuration to the fully narrowed configuration) can be between about 6 cm and about 14 cm, such as between 6 cm and about 8 cm or between about 12 cm and about 14 cm.

In some implementations, the actuating assembly 200 can include a housing 208 that houses the adjustment mechanism 206 and at least partially houses the first and second actuating devices 202, 204. In the illustrated implementation, the first and second actuating devices 202, 204 are configured to move relative to the housing 208 as the adjustment mechanism 206 is moved between various configurations, which allows the actuating assembly 200 to be adjusted in length.

In certain implementations, the actuating assembly 200 includes a locking mechanism (not shown) for locking the actuating assembly 200 at a desired length for the user. The locking mechanism can include any elastic push button (similar to mechanisms on assistive aids such as crutches or walkers), a wedge insert that could be inserted into the actuating assembly 200 to prevent movement of the actuating devices 202, 204, a medial-lateral clamp, a ratcheting mechanism that regulates the rotation of the threaded rods 234, 236, or take any other suitable form such as any form for a locking mechanism described in the present application. In some implementations, the locking mechanism can include a protrusion or member that is configured to engage the gear 238 when in a locked configuration to prevent rotation of the gear 238, and that is configured to be disengaged from the gear 238 when in an unlocked configuration to allow for rotation of the gear 238.

Referring to FIGS. 11-17, an example actuating assembly 300 for powered orthosis includes a first actuating device 302, a second actuating device 304, and an adjustment mechanism 306 connected to both of the first and second actuating devices. The first and second actuating devices 302, 304 can take any suitable form that is capable of supplying an output torque to the hip(s), knee(s), ankle(s), or any combination of the hip(s), knee(s), and ankle(s) of a user. For example, the first and second actuating devices 302, 304 can take the form of any of the actuating devices described in the '234 patent, which is incorporated herein by reference in its entirety. In various implementations, the actuating assembly 300 can include a housing 308 that at least partially houses one or more of the first actuating device 302, the second actuating device 304, and the adjustment mechanism 306.

The first actuating device 302 can have a first actuating arm (not shown) that engages a hip region of a user, and the second actuating device 304 has a second actuating arm (not shown) that engages a knee region of the user. The first actuating arm can have a rotational axis 314 that is configured to align with a rotational axis of the user's hip, and the second actuating arm can have a rotational axis 316 that is configured to align with a rotational axis of the user's knee.

The adjustment mechanism 306 is configured to move the first and second actuating devices 302, 304 relative to each other such that the rotational axes 314, 316 of the corresponding actuating arms move relative to each other. That is, the adjustment mechanism 306 allows for adjustment of the length L (FIG. 11) between the rotational axes 314, 316. This adjustment capability is advantageous because it allows for adjustment of the actuating assembly 300 based on the growth of a user. For example, members the pediatric population typically grow significantly between ages of 6 and 11 and, because the rotational axes 314, 316 of the actuating arms are to be substantially aligned with the rotational axes of the user's hip and knee, respectively, the adjustment mechanism 306 allows for adjustment of the length L between the rotational axes 314, 316 to account for such growth. The length L can be adjusted to be between about 26 cm and about 40 cm, such as between about 29 cm and about 37 cm.

Figure 12:
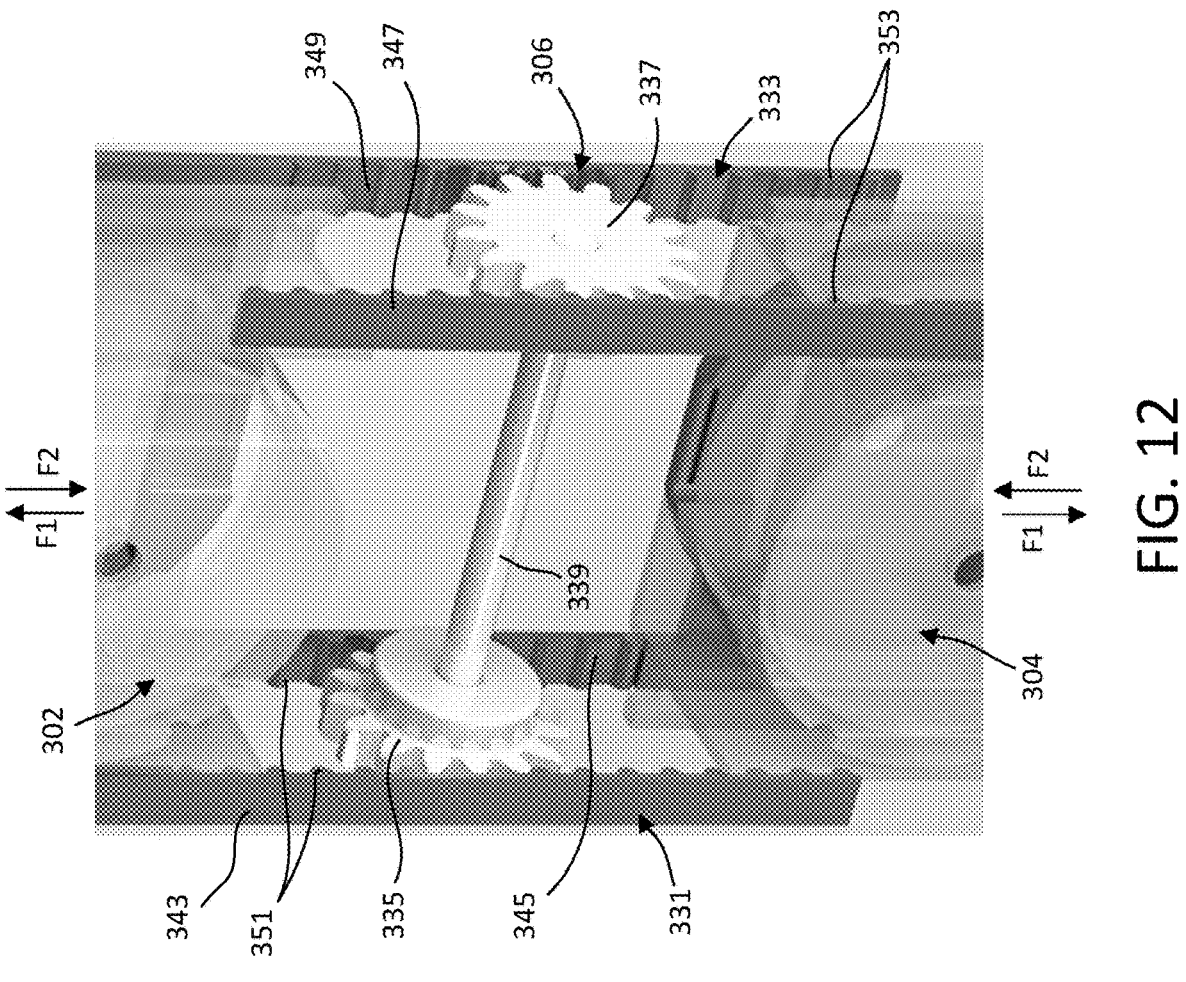
FIG. 12 is a magnified perspective view of the adjustment mechanism of FIG. 11.
Figure 11:
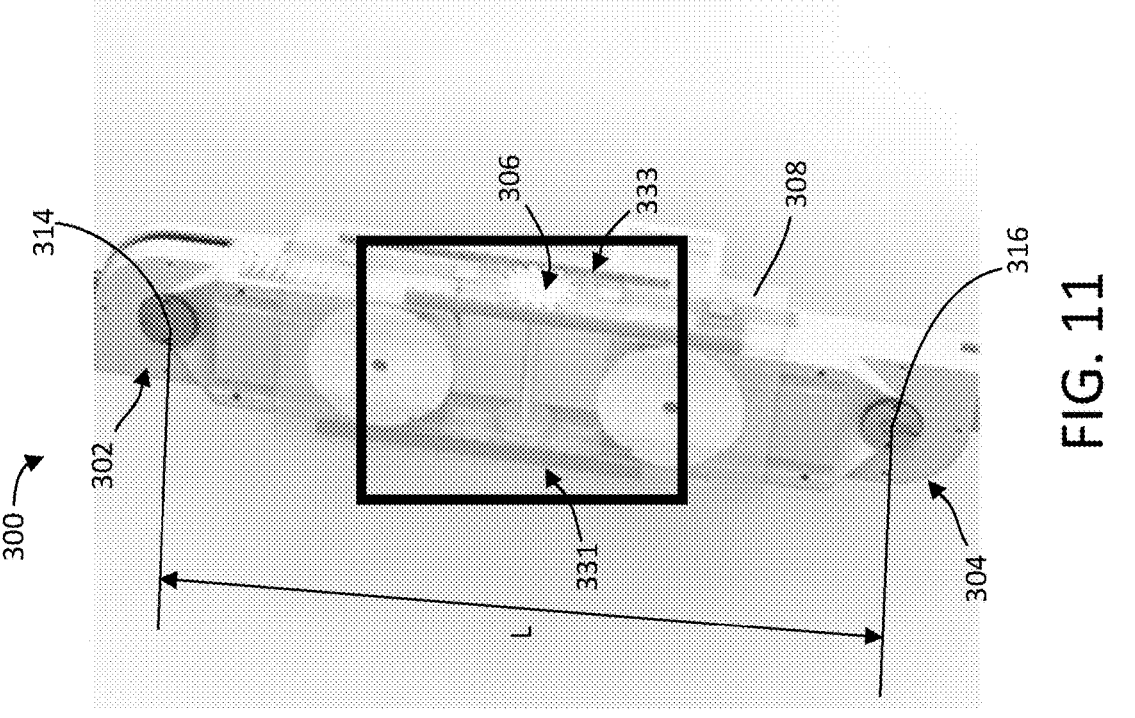
FIG. 11 is a perspective view of another example actuating assembly having an example adjustment mechanism for moving the actuating assembly between narrowed and extended configurations.

Referring to FIGS. 11 and 12, in the illustrated implementation, the adjustment mechanism 306 is a dual rack and pinion mechanism that includes a first rack 331, a second rack 333, a first gear 335 operatively connected to the first rack 331, a second gear 337 operatively connected to the second rack 333, and a rod 339 connected to each of the first and second gears. The adjustment mechanism 306 is configured such that a user can lengthen the actuating assembly 300 by creating an outward force F1 on one or both of the actuating devices 302, 304, and a user can shorten the length of the actuating assembly by creating an inward force F2 on one or both of the actuating devices 302, 304.

Referring to FIG. 12, in the illustrated implementation, the first rack 331 has a first member 343 fixedly connected to the first actuating device 302 and slidably connected to the second actuating device 304, and the first rack 331 has a second member 345 fixedly connected to the second actuating device 304 and slidably connected to the first actuating device 302. The second rack 333 can have a first member 347 fixedly connected to the second actuating device 304 and slidably connected to the first actuating device 302, and the second rack 333 can have a second member 349 fixedly connected to the first actuating device 302 and slidably connected to the second actuating device 304. In various implementations, the members 343, 345 of the first rack 331 are fixedly connected to opposite sides of the first and second actuating devices 302, 304 as compared to the members 347, 349 of the second rack 333. While the illustrated example shows the first and second racks 331, 333 being connected to the actuating devices 302, 304 as described above, it should be understood that the first and second racks 331, 333 can be connected to the actuating devices in any suitable way that allows for the first and second actuating devices 302, 304 to be moved and repositioned relative to each other.

Still referring to FIG. 12, the first gear and second gears 335, 337 are operatively connected to the first and second racks 331, 333, respectively, such that movement of the racks 331, 333 cause the gears 335, 337 to rotate. For example, each member 343, 345 of the first rack 331 can have a plurality of teeth 351 that cause the first gear 335 to rotate as the actuating devices 302, 304 are moved relative to each other, and each member 347, 349 of the second rack 333 can have a plurality of teeth 353 that cause the second gear 337 to rotate as the actuating devices 302, 304 are moved relative to each other. The rod 339 can be connected to the first gear 335 and the second gear 337 such that each of the gears 335, 337 can rotate independently relative to the rod 339. The connection between the gears 335, 337 and the corresponding racks 331, 333 along with the connection between the gears 335, 337 via the rod 339 stabilizes the adjustment mechanism 306 and keeps the adjustment mechanism 306 in alignment as the length L (FIG. 11) of the actuating assembly 300 is being adjusted. In various implementations, these connections maintain the rod 339 in a substantially central position relative to the first and second actuating devices 302, 304.

Figure 13:
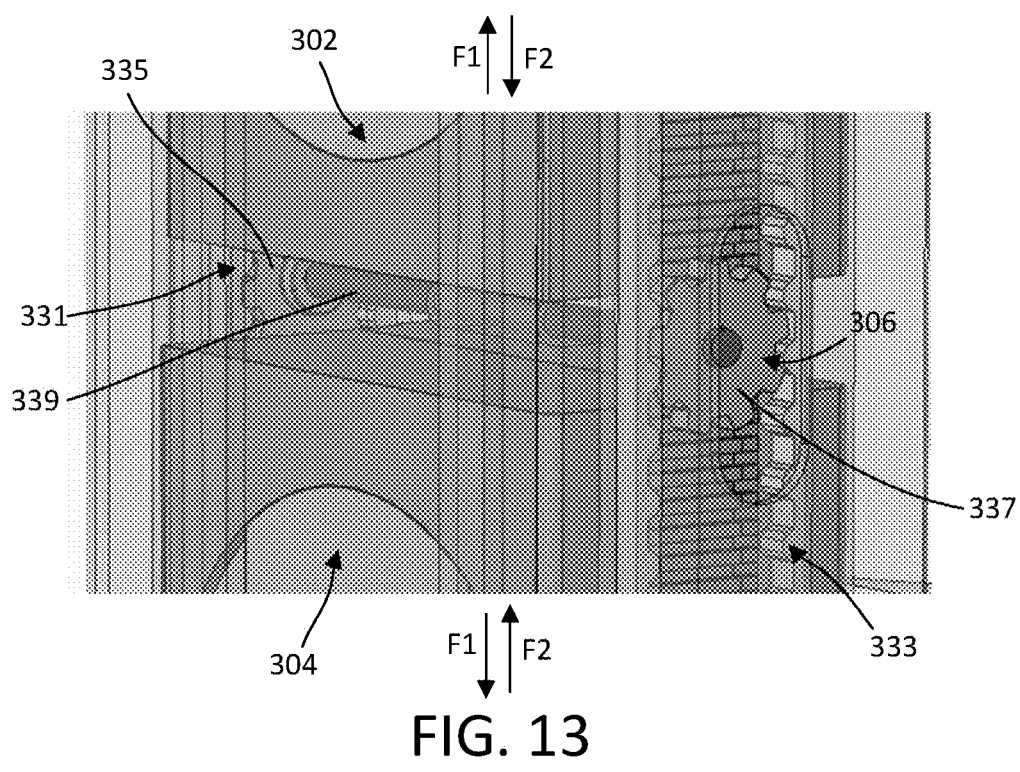
FIG. 13 illustrates a perspective view of the adjustment mechanism in FIG. 11, where the adjustment mechanism is in a first configuration.
Figure 14:
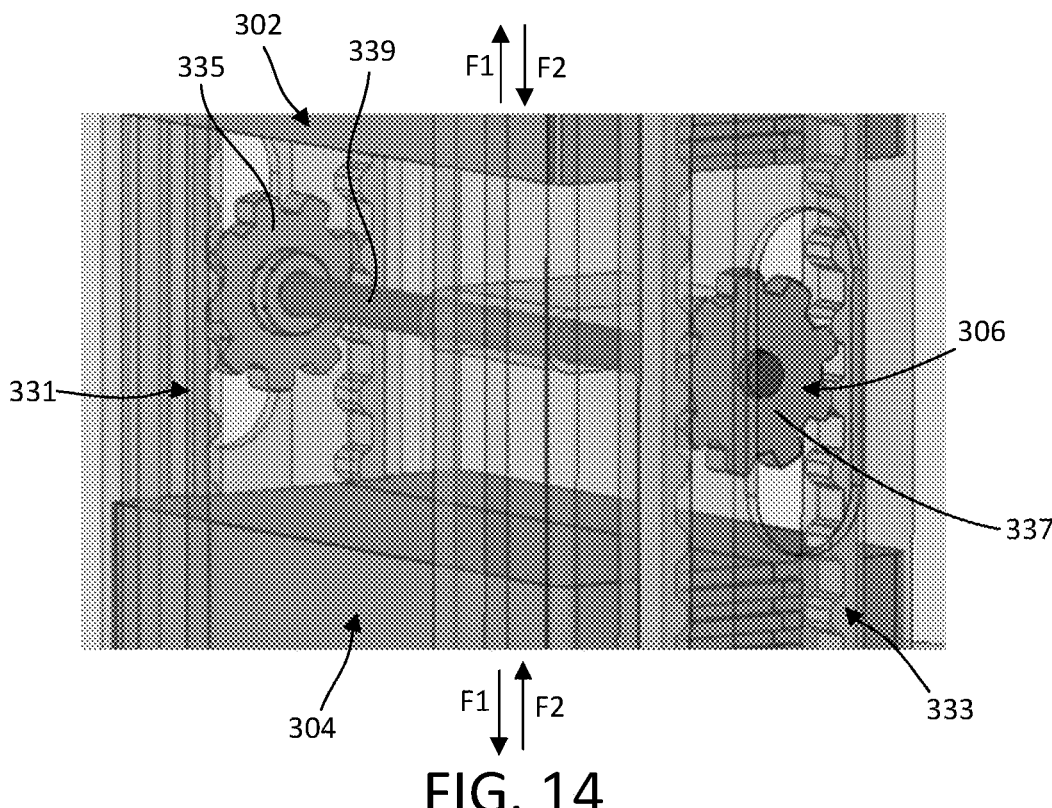
FIG. 14 illustrates a perspective view of the adjustment mechanism of FIG. 11, where the adjustment mechanism is in a second configuration.

Referring to FIG. 13, the adjustment mechanism 306 is shown in a first configuration that causes the actuating assembly 300 (FIG. 11) to be in a substantially narrowed configuration. When in the first configuration, the actuating devices 302, 304 are proximate the rod 339. Referring to FIG. 14, providing an outward force F1 to the first actuating device 302 causes the first member 343 (FIG. 12) of the first rack 331 to move relative to the second actuating device 304. This movement of the first member 343 causes the teeth 351 to engage the first gear 335 such that the first gear 335 moves in a clockwise direction, and this rotation of the first gear 335 causes the first gear 335 to engage the teeth 351 of the second member 345 (FIG. 12) such that the second member 345 (and the fixedly connected second actuating device 304) moves in an outward direction. Still referring to FIG. 14, providing an outward force F1 to the second actuating device 304 causes the first member 347 (FIG. 12) of the second rack 333 to move relative to the first actuating device 302. This movement of the first member 347 causes the teeth 353 to engage the second gear 337 such that the second gear 337 moves in a counterclockwise direction, and this rotation of the second gear 337 causes the second gear 337 to engage the teeth 353 of the second member 349 (FIG. 12) such that the second member 349 (and the fixedly connected first actuating device 302) moves in an outward direction.

While FIGS. 13 and 14 show the adjustment mechanism 306 being moved from a narrowed configuration to an extended configuration, it should be understood that the adjustment mechanism 306 can be narrowed from any configuration by providing an inward force F2 to one or both of the first and second actuating devices 302, 304 until it reaches the fully narrowed configuration. The adjustment mechanism 306 can also be extended from any configuration by providing the outward force F1 to one or both of the first and second actuating devices until it reaches the fully extended configuration. It should also be understood that the adjustment mechanism 306 can be stopped such that the actuating assembly can be at any length between the fully narrowed configuration and the fully extended configuration.

The length L (FIG. 11) extending between the rotational axis 314 of the first actuating arm of the first actuating device 302 and the rotational axis 316 of the second actuating arm of the second actuating device 304 may have a length of between about 26 cm and about 30 cm, such as between about 26 cm and about 27 cm or between about 29 cm and about 30 cm, when the actuating assembly 300 is in a fully narrowed (or shortest) configuration. This length L may be between about 36 cm and about 40 cm, such as between about 36 cm and about 37 cm or between about 39 cm and about 40 cm, when the actuating assembly 300 is in a fully extended (or longest) configuration. In certain implementations, the adjustable length of the adjustment mechanism 306 (i.e., the difference between the length L when in the fully extended configuration to the fully narrowed configuration) can be between about 6 cm and about 14 cm, such as between 6 cm and about 8 cm or between about 12 cm and about 14 cm.

In certain implementations, the actuating assembly 300 can include a locking mechanism 322 for locking the actuating assembly 300 at a desired length for the user. The locking mechanism 322 can include any elastic push button (similar to mechanisms on assistive aids such as crutches or walkers), a wedge insert that could be inserted into the actuating assembly 300 to prevent movement of the actuating devices 302, 304, a medial-lateral clamp, a ratcheting mechanism that regulates the rotation of the gears 335, 337, or take any other suitable form such as any form for a locking mechanism described in the present application.

Figure 15:
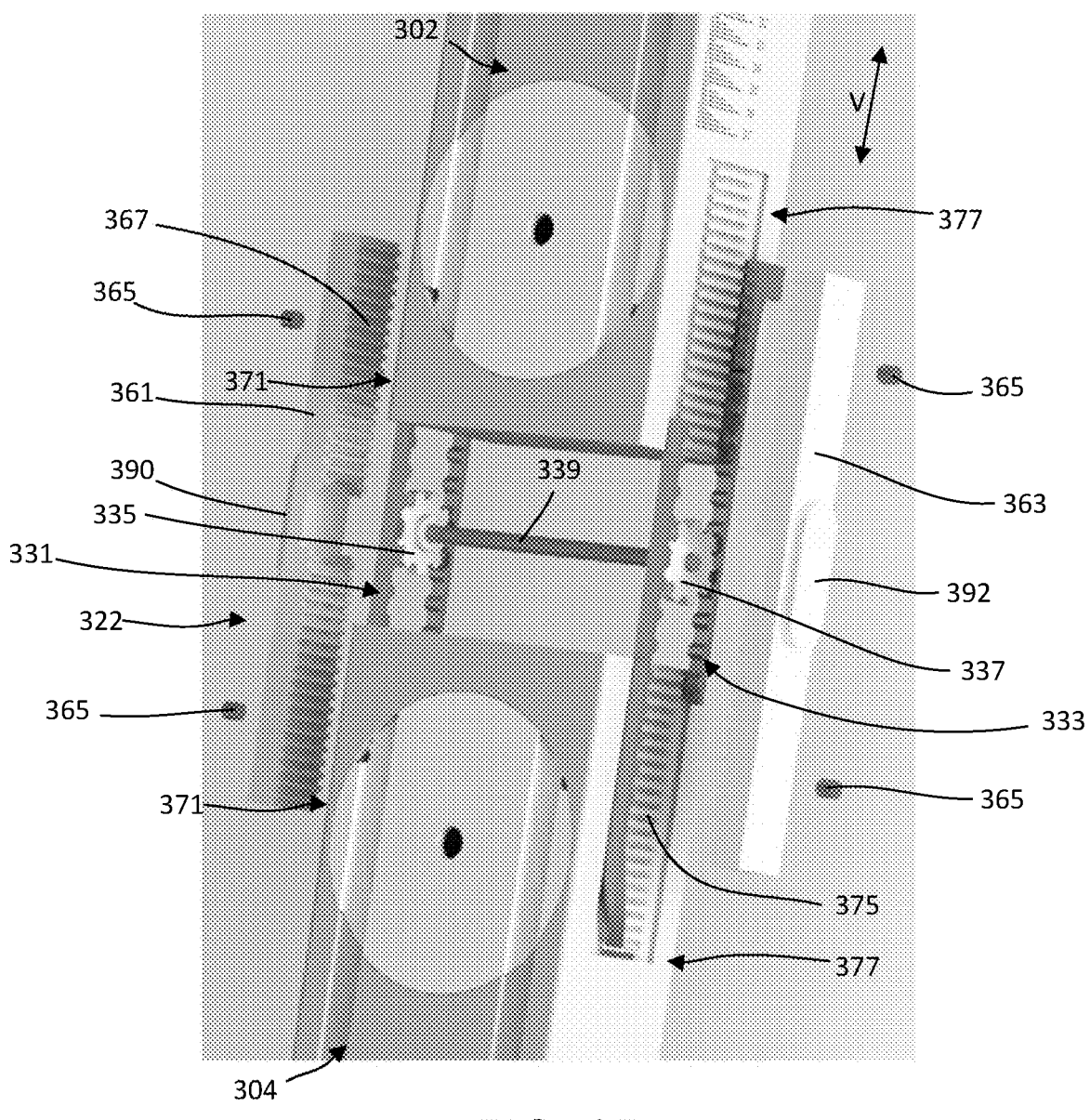
FIG. 15 is a perspective view of the actuating assembly of FIG. 11 having an example locking mechanism.
Figure 16:
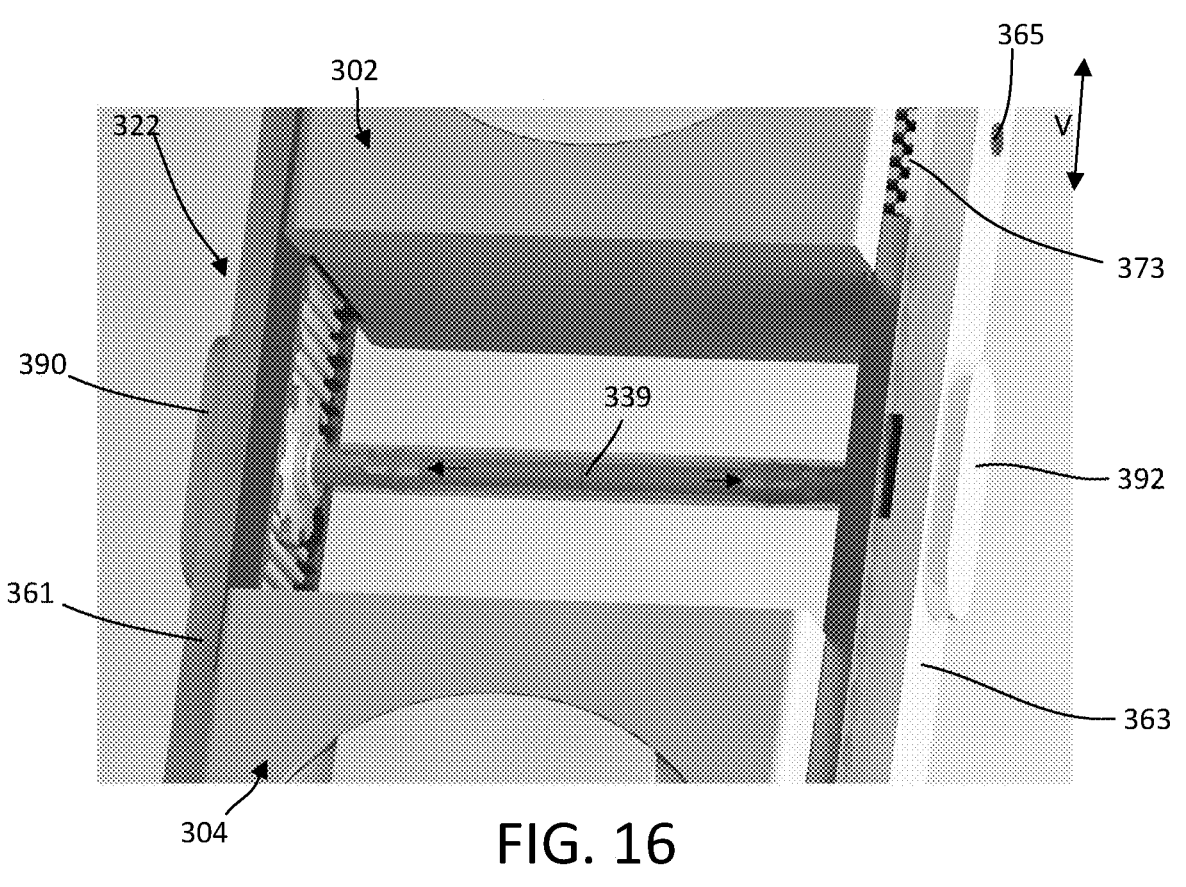
FIG. 16 illustrates a perspective view of the actuating assembly of FIG. 15, where the locking mechanism is in an unlocked configuration.
Figure 17:
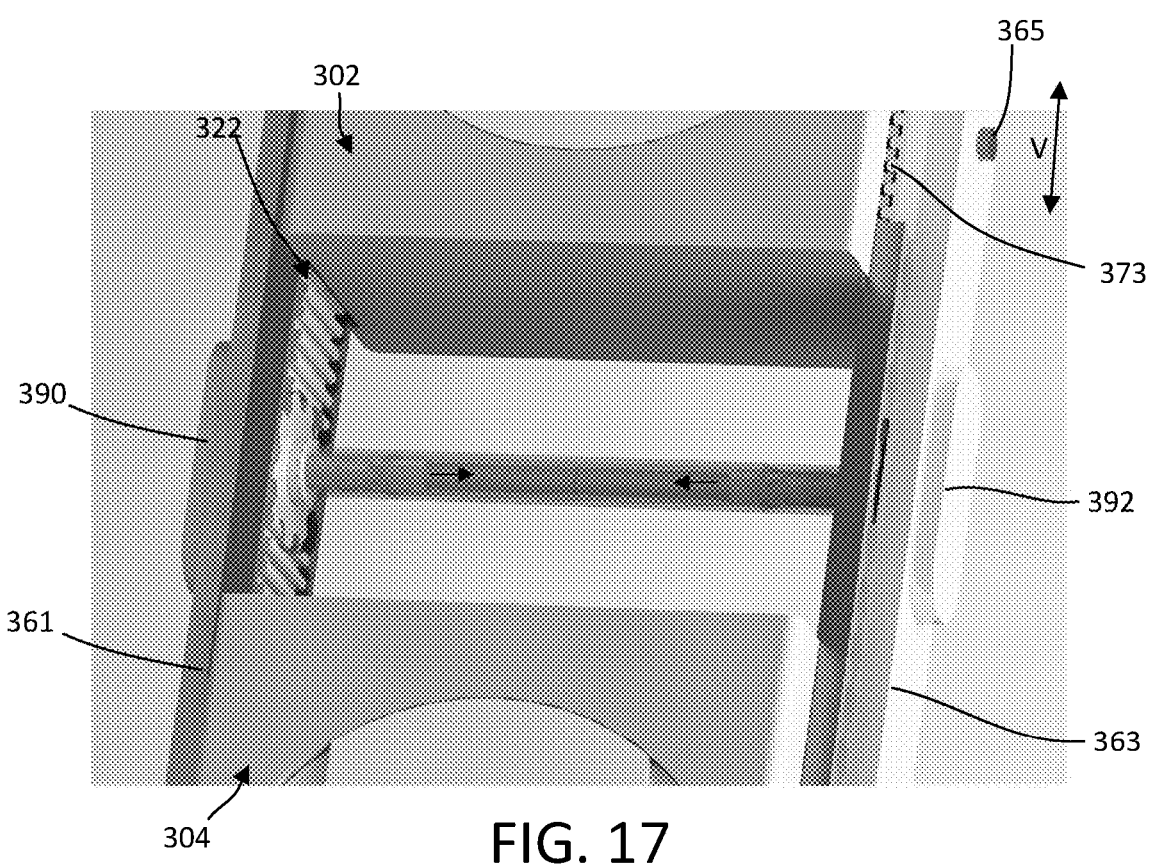
FIG. 17 illustrates a perspective view of the actuating assembly of FIG. 15, where the locking mechanism is in a locked configuration.

Referring to FIGS. 15-17, in some implementations, the locking mechanism 322 can include the rod 339, a first clamp 361, a second clamp 363, and a plurality of spring and dowel assemblies 365. The first clamp 361 has teeth 367 that are configured to engage with teeth (not shown) on a first side 371 of each of the first and second actuating devices 302, 304, and the second clamp 363 has teeth 373 (FIGS. 16-17) that are configured to engage with teeth 375 on a second side 377 of the first and second actuating devices 302, 304. When the locking mechanism 322 is in a locked configuration, the teeth 367, 373 of the first and second clamps 361, 363 intersect with the teeth of the first and second actuating devices 302, 304, which prevents movement of the first and second actuating devices 302, 304 in inward and outward in the vertical direction V. In some implementations, the first and second clamps 361, 363 provide a clamping force on the actuating devices 302, 304. In other implementations, while the teeth 367, 373 of the clamps 361, 363 are intersected with the teeth 369, 375 of the actuating devices 302, 304 to prevent movement of the actuating devices 302, 304 in the direction V, the first and second clamps 361, 363 do not provide a clamping force (or at least a significant clamping force) on the actuating devices 302, 304.

Figures 18, 19:
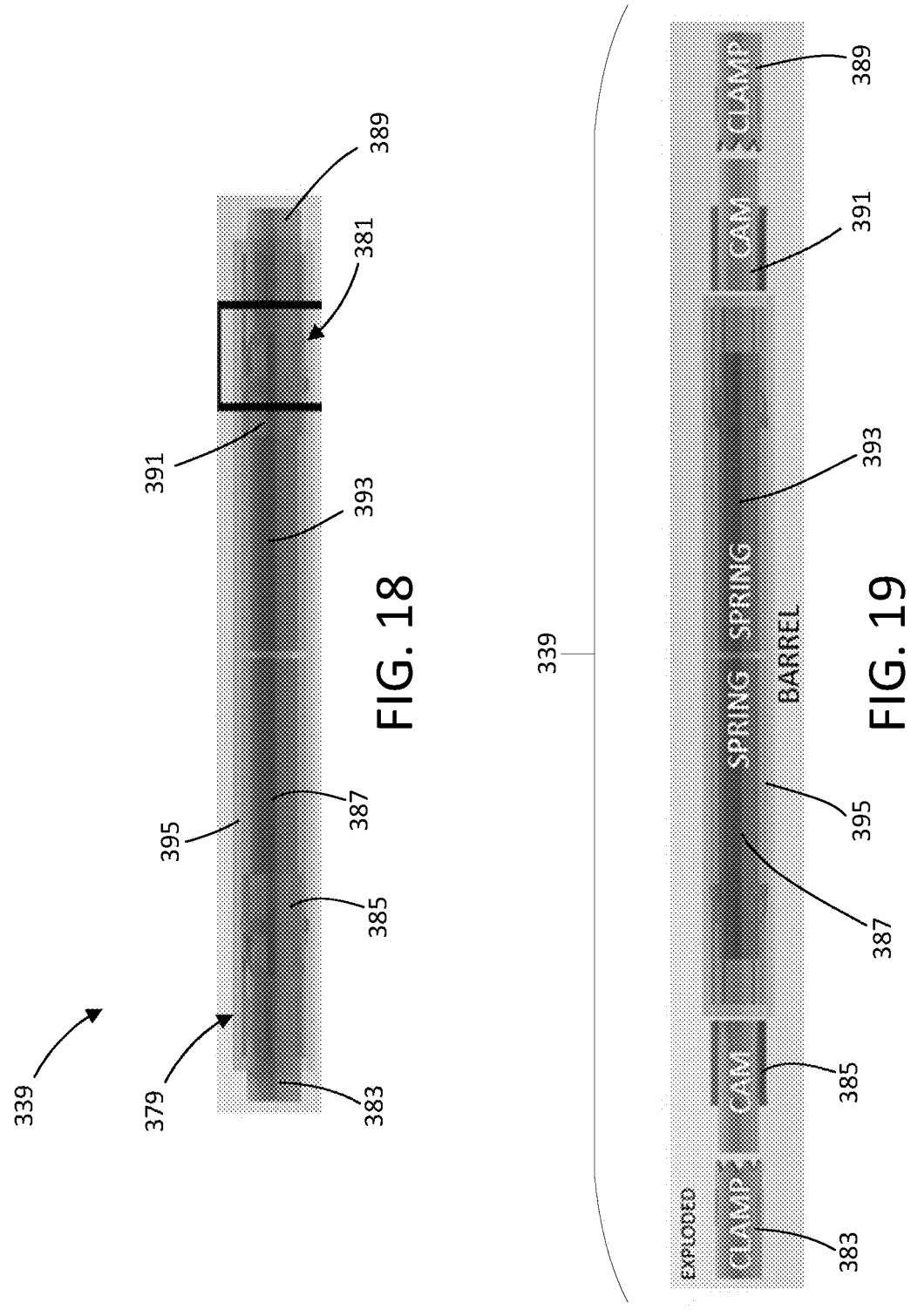
FIG. 18 illustrates a front view of an example rod for the adjustment mechanism and locking mechanism of FIGS. 15-17.
FIG. 19 illustrates an exploded front view of the rod of FIG. 18.

In the illustrated implementation, the rod 339 allows for the locking mechanism 322 to be moved between an unlocked configuration (as shown in FIG. 16) and a locked configuration (as shown in FIG. 17). That is, the rod 339 is movable between a compressed position in which the locking mechanism 322 is in the locked configuration and an expanded position in which the locking mechanism 322 is in the unlocked configuration. Referring to FIGS. 18-19, the rod 339 can have a housing 395, a first spring-loaded end 379 that is connected to the first clamp 361 (FIGS. 15-17), and a second spring-loaded end 381 that is connected to the second clamp 363 (FIGS. 15-17). The spring-loaded ends 379, 381 allow for the rod 339 to move between compressed and expanded configurations.

The spring-loaded ends 379, 381 can act similar to spring-loaded pens in moving between the compressed and expanded positions. For example, the first spring-loaded end 379 of the rod 339 includes a first clamp member 383, a first cam member 385, and a first spring 387, and the second spring-loaded end 381 of the rod 339 includes a second clamp member 389, a second cam member 391, and a second spring 393. The first and second clamp members 383, 389 are configured to be compressed by a user to engage the first and second cam members 385, 391, respectively. In the illustrated example, the first and second clamps 361, 363 of the locking mechanism 322 each have a button 390, 392 that are connected to the corresponding clamp member 383, 389 of the rod 339 such that a user can engage the buttons 390, 392 to cause the clamp members 383, 389 to compress and engage the cam members 385, 391. However, it should be understood that the actuating assembly 300 can include any suitable means that allows a user to engage and compress the clamp members 383, 389 of the rod 339.

Each compression of the clamp members 383, 389 causes the clamp members 383, 389 to engage the cam members 385, 391, which causes the cam members 385, 391 to rotate relative to the clamp members 383, 389 prior to coming to rest in a position relative to the clamp members 383, 389. This rotation of the cam members 385, 391 allows the rod 339 to be moved between the compressed and expanded positions. That is, alternating resting positions of the clamp members 383, 389 and the corresponding cam members 385, 391 cause the rod 339 to alternate between the compressed and expanded positions, and each engagement between the clamp members 383, 389 and the corresponding cam members 385, 391 causes the clamp members 383, 389 to move between these alternating resting positions.

Figure 15A:
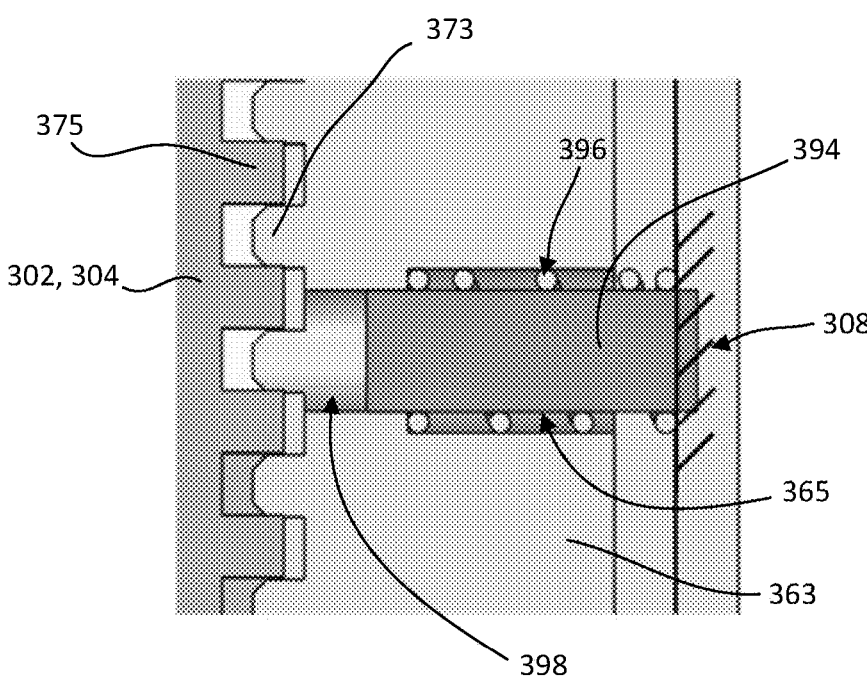
FIG. 15A illustrates an engagement between an example spring and dowel assembly and a clamp of an actuating assembly when the actuating assembly is in a locked configuration.
Figure 15B:
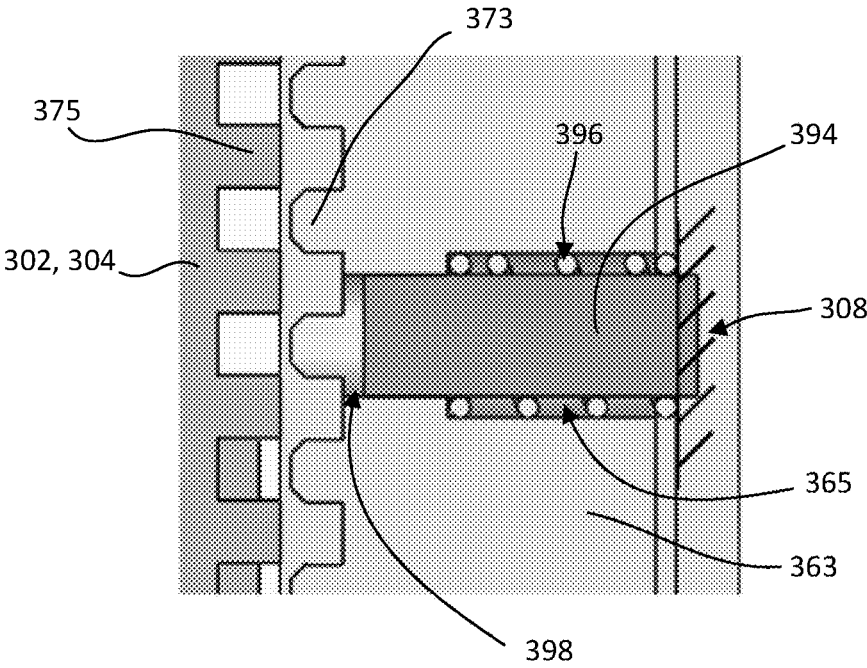
FIG. 15B illustrates an engagement between the example spring and dowel assembly and the clamp of FIG. 15A when the actuating assembly is in an unlocked configuration.

The spring and dowel assemblies 365 are configured to apply an inward force to the first and second clamps 361, 363 to maintain an engagement between teeth 367, 373 of the clamps 361, 363 and the teeth 369, 375 of the actuating devices 302, 304. That is, this inward force prevents the clamps 361, 363 from moving outward while the actuating assembly 300 is in a locked configuration. Referring to FIGS. 15A and 15B, in various examples, each of the spring and dowel assemblies 365 can include a dowel member 394 and a spring 396, which can be at least partially disposed within a corresponding clamp of the first and second clamps 361, 363. The illustrated example shows a spring a dowel assembly 365 that is disposed within the clamp 363. The clamp 363 can include a channel 398 that allows for the dowel member 394 to move within the clamp 363. The dowel member 394 is configured to guide the clamp 363 during movement of the actuating assembly 300 between the locked and unlocked configurations.

Referring to FIG. 15A, the spring 396 is in a normally expanded configuration, which causes an engagement between the spring and dowel assembly 365 and a housing 308 of the actuation assembly 300. This engagement creates a force F1 on the clamp 363 that causes the teeth 373 of the clamp to engage the teeth 375 of the corresponding actuating device 302, 304. Referring to FIG. 15B, when a force F2 is provided to the clamp 363 due to the actuating assembly 300 being moved to the unlocked configuration (e.g., via the rod 339 being moved to the expanded position), the engagement between the housing 308 and the spring and dowel assembly 365 causes the spring 396 to move to a narrowed configuration. Referring again to FIG. 15A, when the actuating assembly 300 is moved back to the locked configuration (e.g., via the rod 339 being moved to the narrowed position), the engagement between the housing 308 and the spring and dowel assembly 365 causes the spring to create the force F1 on the clamp 361 such that the teeth 373 of the clamp to engage the teeth 375 of the corresponding actuating device 302, 304. While the spring and dowel assembly 365 is shown with clamp 363, it should be understood that the spring and dowel assembly 365 works similarly with clamp 361. Also, while the spring and dowel assembly 365 is shown engaging a housing 308 of the actuating assembly 300, it should be understood that the spring and dowel assembly 365 can be configured to engage any other suitable component of the actuating assembly 300 that allows for the spring and dowel assembly 365 to function as described in the present application.

In some implementations, the actuating assembly 300 can include a housing 308 that houses the adjustment mechanism 306 and at least partially houses the first and second actuating devices 302, 304. In the illustrated implementation, the first and second actuating devices 302, 304 are configured to move relative to the housing 308 as the adjustment mechanism 306 is moved between various configurations, which allows the actuating assembly 300 to be adjusted in length.

Figure 20:
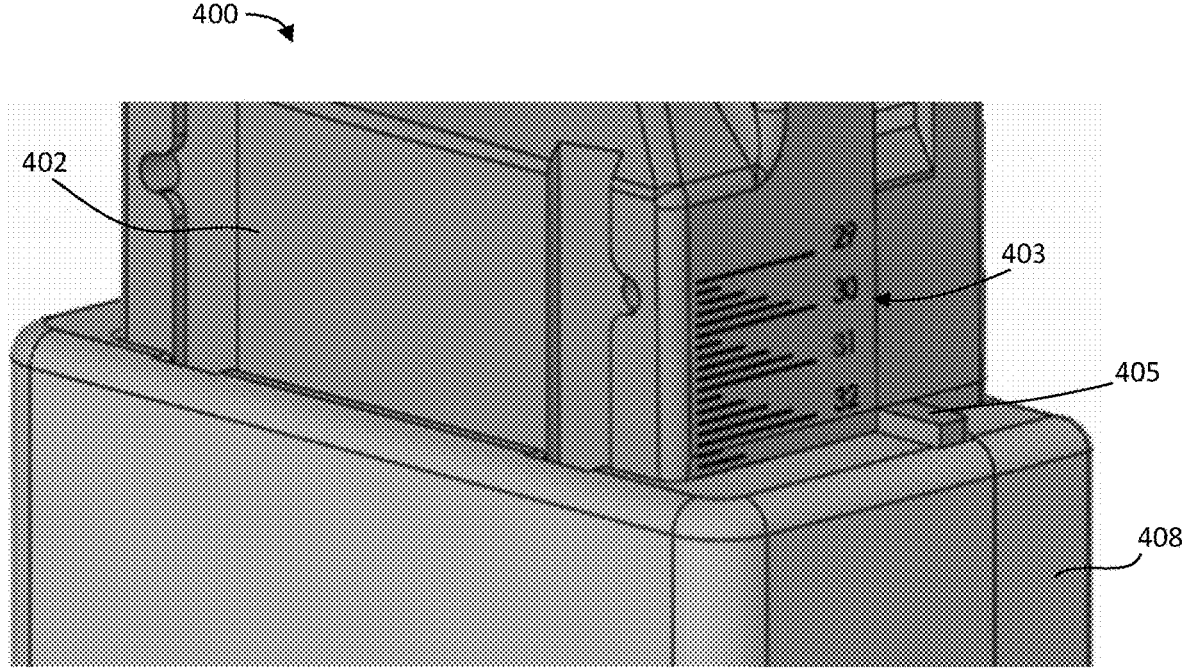
FIG. 20 illustrates a partial view of an example actuating assembly that includes an example length scale.

Referring to FIG. 20, an example length scale 403 for an actuating assembly 400 that is movable between narrowed and extended configurations. The actuating assembly 400 can take any suitable form that is capable of being adjusted between narrowed and expanded configurations, such as, for example, any form described in the present application. The example length scale 403 includes a system of measurement (e.g., United States customary units, International System of Units, or any other suitable system of length measurement) that allows a user to determine a length of the actuating assembly 400. The length being illustrated by the length scale 403 can be the length between the axes of rotation for each of the actuating devices, the total length of the actuating assembly 400, the length between the actuating devices, or any other suitable length that allows a user to adjust the actuating assembly 400 as desired to fit a user.

In the illustrated implementation, the length scale 403 is disposed on a first actuating device 402, and the housing 408 includes a marker 405 that is aligned with the length scale 403. The determined length of the actuating assembly 400 is decided by the position of the marker 408 relative to the length scale 403. That is, as the actuating assembly 400 is moved between various extended and narrowed position, the actuating device 402 is moved relative to the housing 408, and this movement changes the position of the marker 405 relative to the length scale 403. When the marker 405 shows that the actuating assembly 400 is at a desired length for a user, the actuating assembly 400 can be locked or otherwise maintained in that configuration by any means described in the present application.

While the various implementations for all of the actuating assemblies described herein are described as being directed to an adjustable length actuating assembly for powered orthosis configured to engage a user's hip and knee, it should be understood that the adjustment mechanisms and other components of these actuating assemblies can be used for any other suitable type of actuating assembly for any type of orthosis device (powered or otherwise controlled).

While various inventive aspects, concepts and features of the inventions may be described and illustrated herein as embodied in combination in the exemplary embodiments, these various aspects, concepts and features may be used in many alternative embodiments, either individually or in various combinations and sub-combinations thereof. Unless expressly excluded herein all such combinations and sub-combinations are intended to be within the scope of the present inventions. Still further, while various alternative embodiments as to the various aspects, concepts and features of the inventions, such as alternative materials, structures, configurations, methods, devices and components, alternatives as to form, fit and function, etc. may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the present inventions, even if such embodiments are not expressly disclosed herein.

Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated.

While various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention, the inventions instead being set forth in the appended claims. Descriptions of exemplary methods or processes are not limited to inclusion of all steps as being required in all cases, nor is the order that the steps are presented to be construed as required or necessary unless expressly so stated.

The invention claimed is:

1. An actuating assembly for orthosis, comprising:

a first actuating device configured to provide an output torque to a first portion of a user;

a second actuating device configured to provide an output torque to a second portion of the user; and an adjustment mechanism connected to the first actuating device and the second actuating device, wherein the adjustment mechanism is configured to adjust a distance between the first and second actuating devices, the adjustment mechanism comprising:

a first scissor arm having a first arm portion and a second arm portion that are pivotally connected at a first connection point, wherein the first arm portion is connected to the first actuating device and the second arm portion is connected to the second actuating device;

a second scissor arm having a third arm portion and a fourth arm portion that are pivotally connected at a second connection point, wherein the third arm portion is connected to the first actuating device and the fourth arm portion is connected to the second actuating device;

a first threaded nut connected to the first scissor arm at the first connection point;

a second threaded nut connected to the second scissor arm at the second connection point;

a first threaded rod connected to the first threaded nut such that rotation of the first threaded rod causes the first threaded nut to move along a length of the first threaded rod;

a second threaded rod connected to the second threaded nut such that rotation of the second threaded rod causes the second threaded nut to move along a length of the second threaded rod; and a gear connected to the first and second threaded rods such that rotation of the gear causes the first and second threaded rods to rotate.

2. The actuating assembly according to claim 1, wherein each of the first arm portion and the second arm portion comprise two arm members, and wherein the first threaded nut is disposed between the two arm members of each of the first and second arm portions.

3. The actuating assembly according to claim 1, wherein rotation of the gear in the clockwise direction causes the adjustment mechanism to increase the distance between the first and second actuating devices, and wherein rotation of the gear in the counterclockwise direction causes the adjustment mechanism to decrease the distance between the first and second actuating devices.

4. The actuating assembly according to claim 1, wherein the gear is configured to be rotated by an external tool.

5. The actuating assembly according to claim 1, further comprising a locking mechanism configured to prevent the adjustment mechanism from adjusting the distance between the first and second actuating devices.

\*　\*　\*　\*　\*